United States Patent
Alfaro et al.

(10) Patent No.: US 8,496,137 B2
(45) Date of Patent: Jul. 30, 2013

(54) SOLENOID VALVE ASSEMBLY FOR A DISPENSING SYSTEM

(75) Inventors: Raymund J. Alfaro, Oak Creek, WI (US); Dennis J. Beaumont, Libertyville, IL (US); Thomas P. Gasper, Germantown, WI (US); Sebastian D. Hasik, Antioch, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 257 days.

(21) Appl. No.: 13/030,955

(22) Filed: Feb. 18, 2011

(65) Prior Publication Data

US 2012/0211513 A1   Aug. 23, 2012

(51) Int. Cl.
*B67D 1/00*   (2006.01)

(52) U.S. Cl.
USPC ........ 222/63; 222/402.13; 222/504; 222/647; 222/649; 137/513.5; 251/129.15

(58) Field of Classification Search
USPC ................ 222/4, 52, 61, 63, 639, 644–649, 222/402.1, 402.13, 394, 173, 333, 504; 251/129.15, 117; 137/513.5
See application file for complete search history.

(56) References Cited

U.S. PATENT DOCUMENTS

| | | | |
|---|---|---|---|
| 3,640,312 A | 2/1972 | Bauman et al. | |
| 3,848,775 A * | 11/1974 | Possell | 222/649 |
| 3,873,951 A | 3/1975 | Blake | |
| 3,998,364 A | 12/1976 | Hollander | |
| 4,129,235 A | 12/1978 | Haas | |
| 4,218,940 A | 8/1980 | Main | |
| 5,232,447 A | 8/1993 | Schwarz et al. | |
| 5,370,317 A | 12/1994 | Weston | |
| 5,762,322 A * | 6/1998 | Smith | 251/353 |
| 6,007,561 A | 12/1999 | Bourque et al. | |
| 6,267,297 B1 * | 7/2001 | Contadini et al. | 239/1 |
| 6,783,110 B2 * | 8/2004 | Hirota et al. | 251/129.21 |
| 7,100,889 B2 * | 9/2006 | Purvines et al. | 251/129.15 |
| 7,320,418 B2 * | 1/2008 | Sassoon | 222/649 |
| 7,407,065 B2 * | 8/2008 | Hooks et al. | 222/1 |
| 7,666,169 B2 | 2/2010 | Cowan et al. | |
| 7,938,340 B2 * | 5/2011 | Anderson et al. | 239/337 |
| 2008/0202950 A1 | 8/2008 | Anderson | |
| 2009/0234366 A1 | 9/2009 | Tsai et al. | |
| 2010/0155432 A1 * | 6/2010 | Christianson | 222/402.1 |

FOREIGN PATENT DOCUMENTS

| | | |
|---|---|---|
| WO | 0064770 | 11/2000 |
| WO | 03104109 A1 | 12/2003 |
| WO | 2005020853 | 3/2005 |
| WO | 2007045827 A1 | 4/2007 |

OTHER PUBLICATIONS

PCT/US2012/025169 International Search Report dated Jun. 4, 2012.

* cited by examiner

*Primary Examiner* — Paul R Durand
*Assistant Examiner* — Andrew P Bainbridge

(57) ABSTRACT

A solenoid valve assembly is adapted to control product flow through a dispensing system. The dispensing system includes a housing. A plunger is disposed within the housing and has a first axial surface. A stopper is also disposed within the housing and has a second axial surface facing the first axial surface. At least one flow pathway is provided on at least one of the first and second axial surfaces.

20 Claims, 14 Drawing Sheets

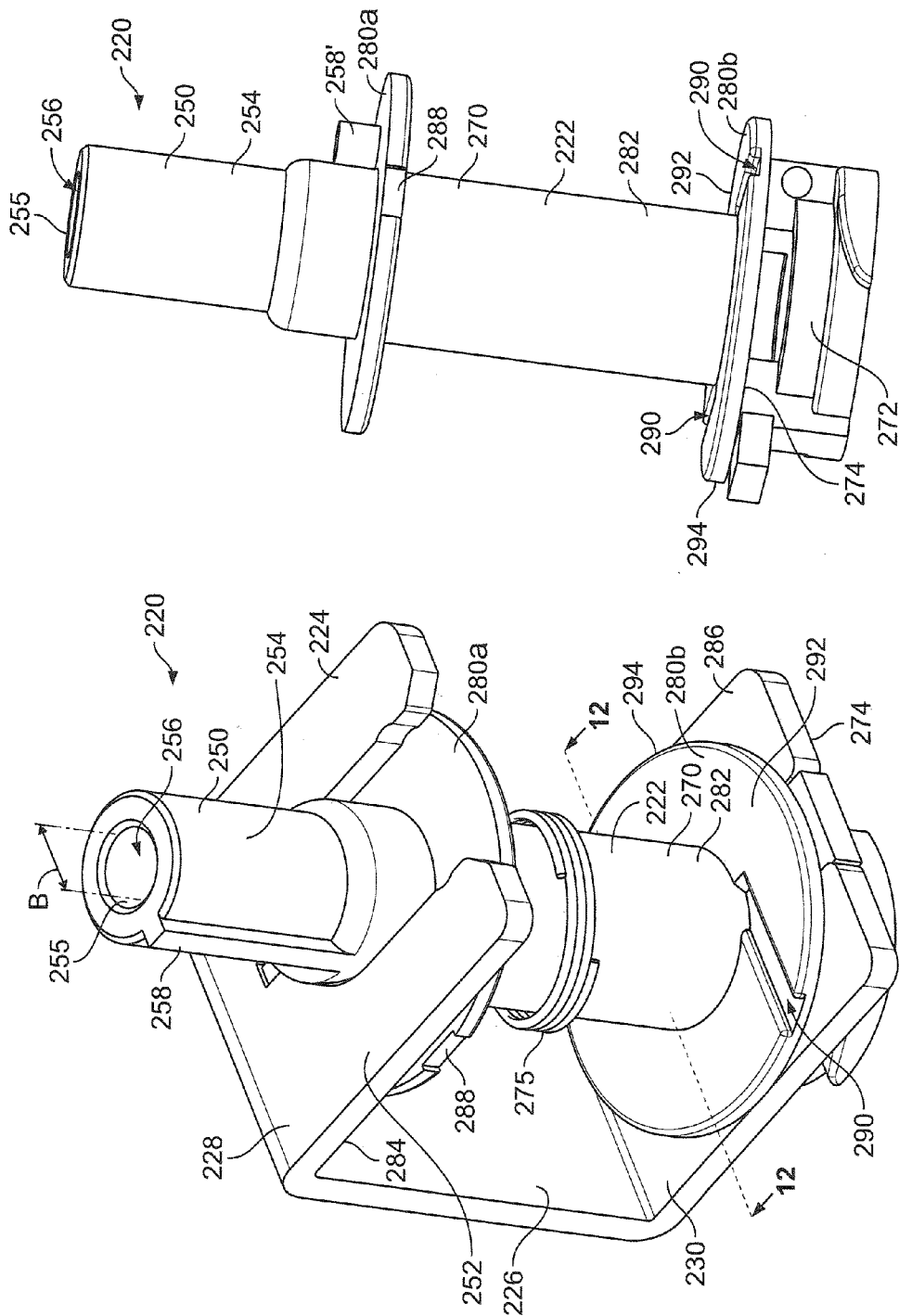

SOLENOID VALVE ASSEMBLY FOR A DISPENSING SYSTEM

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to a method and an apparatus for maintaining fluid flow through a solenoid valve, and more particularly, to utilizing a solenoid valve assembly having at least one non-planar surface in a fluid flow channel thereof.

2. Description of the Background of the Invention

Aerosol containers are commonly used to store and dispense a product such as air freshening agents, deodorants, insecticides, germicides, cleaning agents, nasal decongestants or other nasally-introduced medicaments, bronchodilators or other medicaments delivered to or via the lungs, perfumes, a gel or any other known fluids or substances. The product forced from the container through an aerosol valve by a hydrocarbon or non-hydrocarbon propellant may be mixed or otherwise in contact with the product. Alternatively, a pressurized piston may forcibly eject the product through the aerosol valve. The product released from such containers may be in solid form, liquid form, gas form, and/or some combination or intermediate thereof.

A typical aerosol container comprises a body with an opening at a top end thereof. A mounting cup is crimped to the opening of the container. The mounting cup includes an outer wall that extends upwardly and inwardly from a base of the mounting cup. A pedestal is crimped to and extends upwardly from a central portion of the mounting cup. A valve having a valve stem is carried by the pedestal.

Often, the contents of an aerosol container are dispensed by an actuation system that controls product flow therethrough. One typical apparatus for controlling fluid flow is a solenoid valve. A solenoid valve comprises a solenoid having a core and a valve assembly operated by the solenoid coil. Specifically, electrical power is supplied to the coil, and the resulting magnetic flux moves a spring-loaded armature, thereby moving the armature out of contact with a sealing surface. This movement permits discharge of a product until electrical current is no longer supplied to the solenoid coil, whereupon the armature moves in an opposite direction, thereby returning the armature to the sealed position, terminating product flow.

In automatic actuation systems utilizing solenoid valves, the solenoid valve is typically cycled between on and off states during each of a plurality of duty cycles. Conventionally, the solenoid valve is actuated up to a maximum relatively brief period of time. This is due to the fact that when the solenoid is actuated for longer on times, a planar axial face of the armature may contact a planar top surface of the stopper, thereby forming a seal that partially or fully blocks the flow of product. While limiting on times has been effective to minimize flow interruption, it has been found desirable to provide a system that allows a solenoid valve to be actuated for longer on times. A system is presented herein that allows product to continuously flow during longer activation cycles. Portions of the plunger and/or stopper are made non-planar. The non-planar design ensures consistent flow of the product when the solenoid valve assembly is energized for actuation over any amount of time.

SUMMARY OF THE INVENTION

According to one aspect of the invention, a solenoid valve assembly adapted to control product flow through a dispensing system includes a housing. A plunger is disposed within the housing and has a first axial surface. A stopper is also disposed within the housing and has a second axial surface facing the first axial surface. At least one flow pathway is provided on at least one of the first and second axial surfaces.

According to another aspect of the invention, a product dispensing system includes a container having a product therein, an overcap releasably attached thereto, and a solenoid valve assembly adapted to control product flow through the dispensing system. The solenoid valve assembly includes a housing. A plunger is disposed within the housing and has a first axial surface. A stopper is also disposed within the housing and has a second axial surface facing the first axial surface. At least one flow pathway is provided on at least one of the first and second axial surfaces.

According to a different aspect of the invention, a method of dispensing a product includes the steps of providing a solenoid valve assembly, which includes a housing, a plunger within the housing having a first axial surface, and a stopper within the housing having a second axial surface facing the first axial surface. At least one flow pathway is provided on at least one of the first and second axial surfaces. The method further includes the steps of providing a product within a container in communication with the solenoid valve assembly, providing a switch adapted to control the actuation of the solenoid valve assembly, and activating the switch to dispense the product through the solenoid valve assembly.

Other aspects and advantages of the present invention will become apparent upon consideration of the following detailed description and the attached drawings, in which like elements are assigned like reference numerals.

BRIEF DESCRIPTION OF THE DRAWINGS

FIG. 10 is a top isometric view of a solenoid valve assembly comprising a housing and a C-shaped bracket;

FIG. 11 is an isometric view of the housing of the solenoid valve assembly of FIG. 10;

DETAILED DESCRIPTION OF THE DRAWINGS

Figure 1:
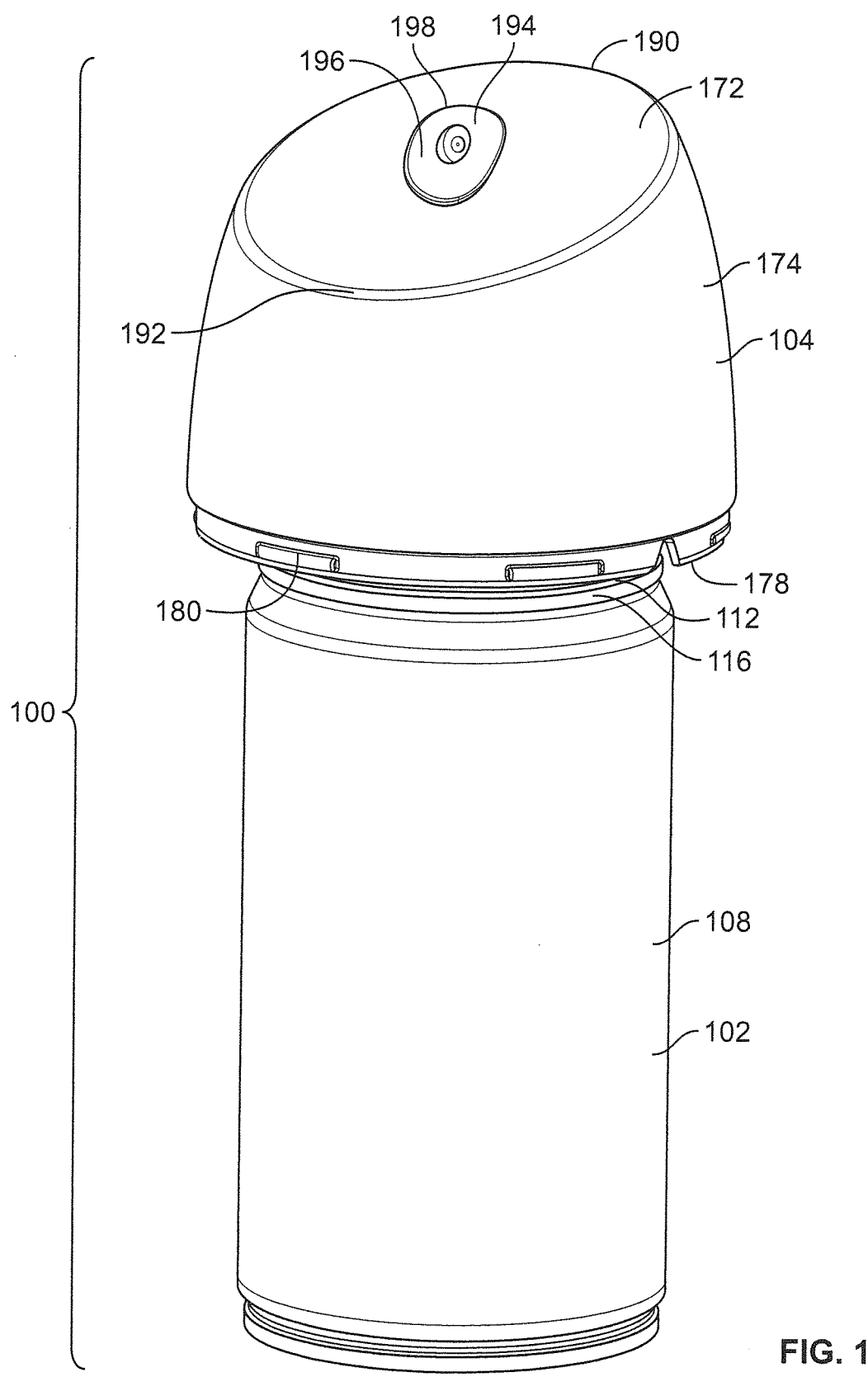
FIG. 1 is an isometric view of one type of aerosol container with an overcap attached thereto.

FIG. 1 depicts a product dispensing system 100 that includes a container 102 and an overcap 104 releasably attached thereto. The container 102 includes a product 106 (see FIG. 3) adapted to be released from the overcap 104. The product 106 may take any form including solid, liquid, gas, or the like. In one embodiment, the product 106 further includes a volatile material dispersed therein. Although a fluid or liquid is discussed in connection with the embodiments disclosed herein, it is contemplated that the product dispensing system 100 may be adapted to release any product as known in the art. Further, although a specific container and overcap are discussed herein, it is anticipated that various alternative containers and overcaps may be used as known in the art. An attachment mechanism (not shown) may be used to secure the overcap 104 to the container 102.

Figure 2:
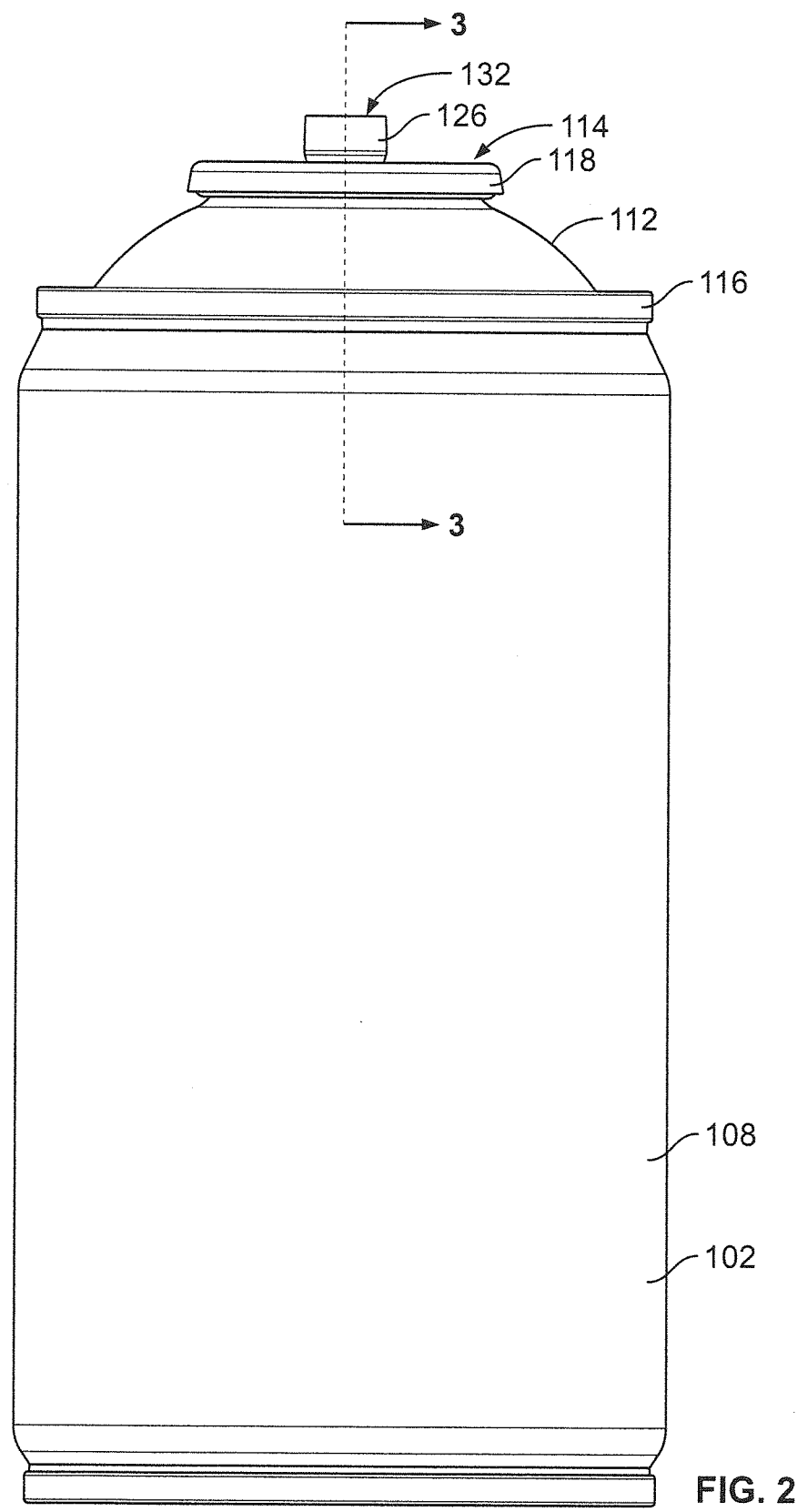
FIG. 2 is a side elevational view of the container of FIG. 1.
Figure 3:
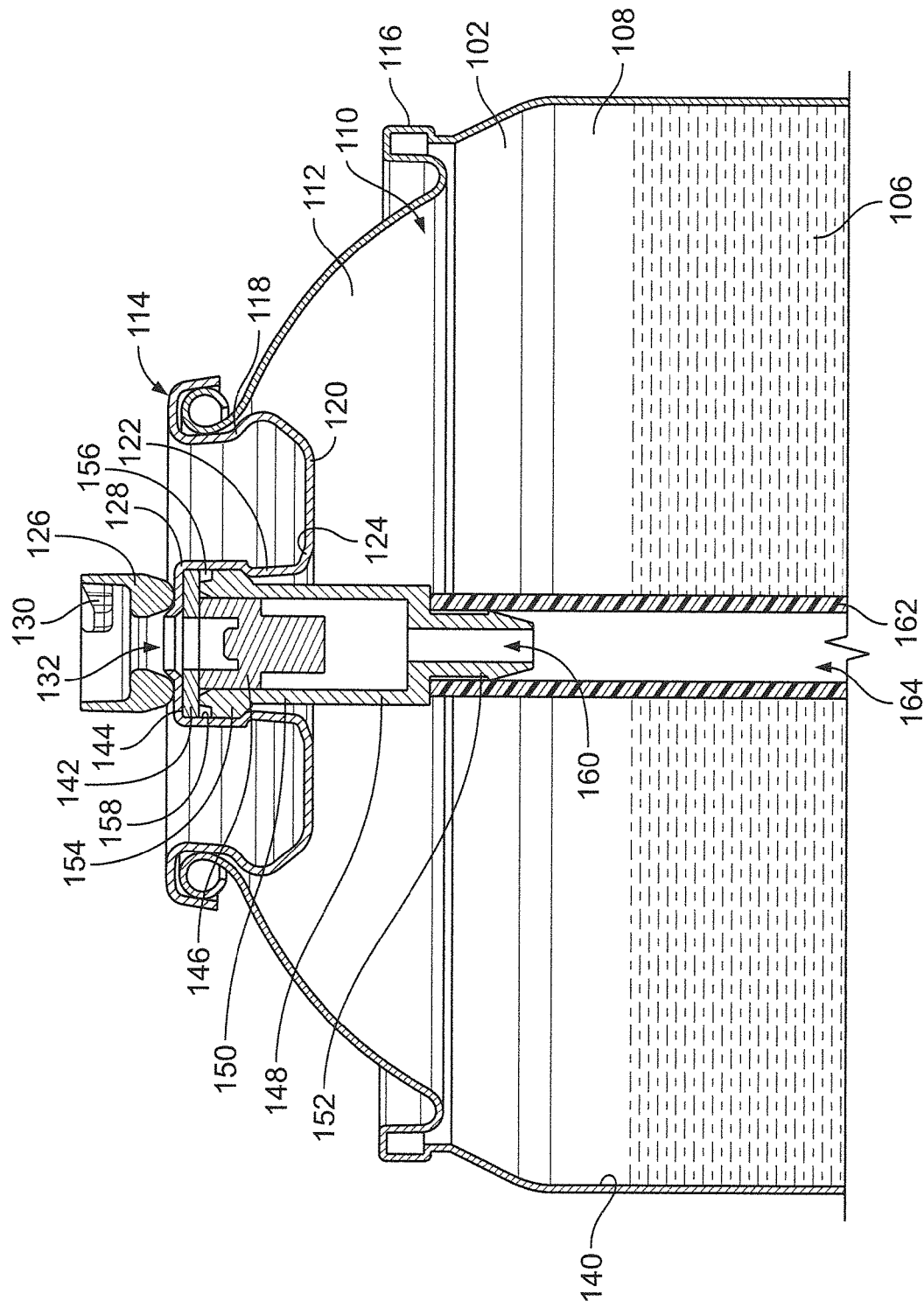
FIG. 3 is a fragmentary cross-sectional view of a top end of the container of FIG. 1 taken generally along the lines 3-3 of FIG. 2.

Referring to FIGS. 1-3, the container 102 comprises a substantially cylindrical body 108 with an opening 110 at a top end 112 thereof. A mounting cup 114 is crimped to a tapered or dome-shaped portion of the container 102, which defines the opening 110. The mounting cup 114 seals the top end 112 of the body 108. A second crimped portion at a bottom end of the dome-shaped portion defines a seam 116. The mounting cup 114 is generally circular-shaped and includes a wall 118 that protrudes upwardly from a base 120 of the mounting cup 114 adjacent the area of crimping. As best seen in FIG. 3, a pedestal 122 extends upwardly from a central portion 124 of the base 120. The pedestal 122 includes an annular extension member 126 disposed on an upper edge 128 thereof that further includes an inwardly projecting protrusion 130. The protrusion 130 is adapted to provide additional surface area for actuation of the product dispensing system 100. The pedestal 122 and the annular extension member 126 define an opening 132 adapted to allow product flow therethrough. The opening 132 is adapted to receive a portion of an actuating member 134, which is described in more detail hereinbelow. The actuating member 134 extends from the overcap 104 and is adapted to be inserted into the opening 132. In one embodiment, the annular extension member 126 extends from the pedestal 122 of the container 102, as shown in FIG. 3. In a different embodiment, the annular extension member 126 extends downwardly from a portion of the overcap 104, for example, from the actuating member 134. In this embodiment, the annular extension member 126 may extend downwardly from the actuating member 134 and mate with the pedestal 122 to form a fluid-tight connection. In still a further embodiment, the annular extension member 126 may be omitted all together from the product dispensing system 100.

Again referring to FIG. 3, the container 102 is adapted to release the product 106 therefrom, which is disposed in an interior portion 140 of the container 102. A valve assembly is typically substantially enclosed in the interior portion 140 of the container 102 and includes a gasket 142 disposed adjacent a top end 144 of the pedestal 122 that circumscribes the opening 132. A plunger valve 146 is disposed directly below the gasket 142 and extends downwardly into the container body 108. A valve housing 148 surrounds the plunger valve 146 and includes an upper wide portion 150 and a lower narrowed portion 152 extending downwardly therefrom. The upper portion 150 includes a bulbous protrusion 154 extending outwardly therefrom adapted to interact with a corresponding groove 156 on an interior wall 158 of the mounting cup 114 to secure the valve housing 148 thereto. The valve housing 148 provides support and a fluid tight seal for the valve 146. The lower narrowed portion 152 extends downwardly from the upper portion 150 and defines a cylindrical chamber 160. A dip tube 162 surrounds the lower narrowed portion 152 and extends downwardly therefrom. The dip tube 162 extends downwardly into the body 108 of the container 102 and defines a dip tube channel 164 therein adapted to allow the product 106 to flow therethrough. Although a specific valve assembly is discussed herein, it is contemplated that any type of valve assembly may be used herein as known to one of skill in the art.

Figure 4:
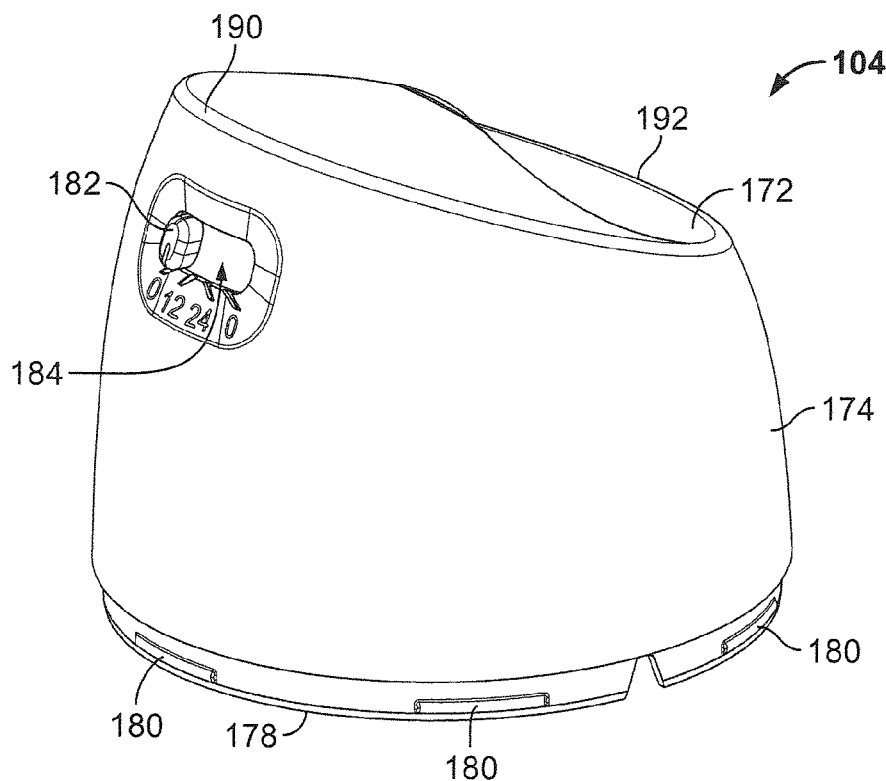
FIG. 4 is an isometric view illustrating an opposite side of the overcap of FIG. 1.
Figure 5:
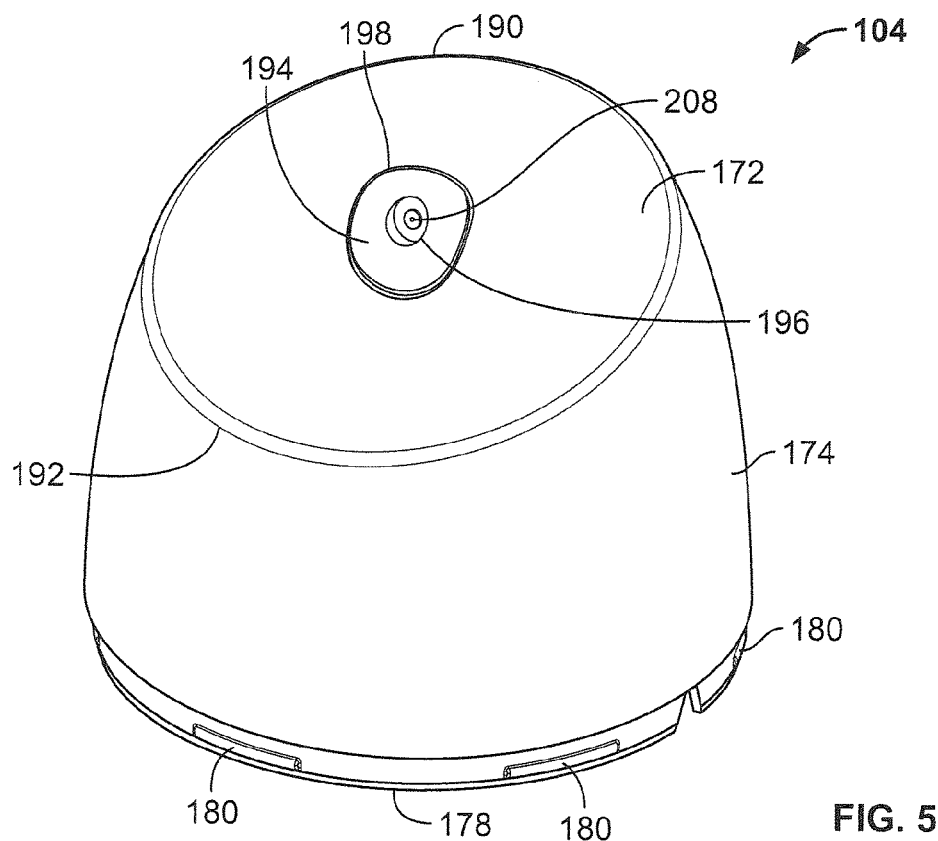
FIG. 5 is an isometric view of the overcap of FIG. 1.
Figure 6:
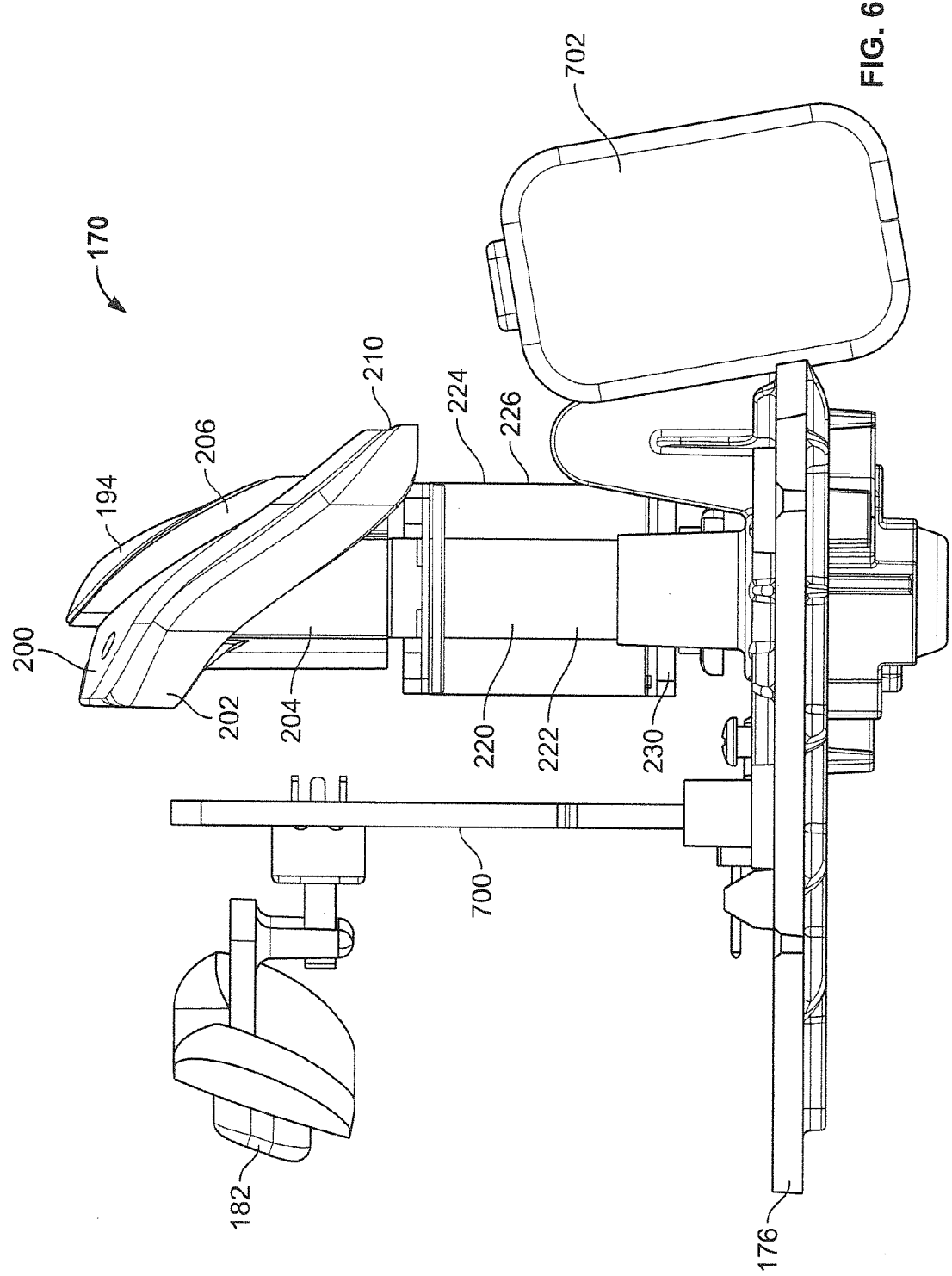
FIG. 6 is a side elevational view of the overcap of FIG. 1 with structures removed therefrom.
Figure 7:
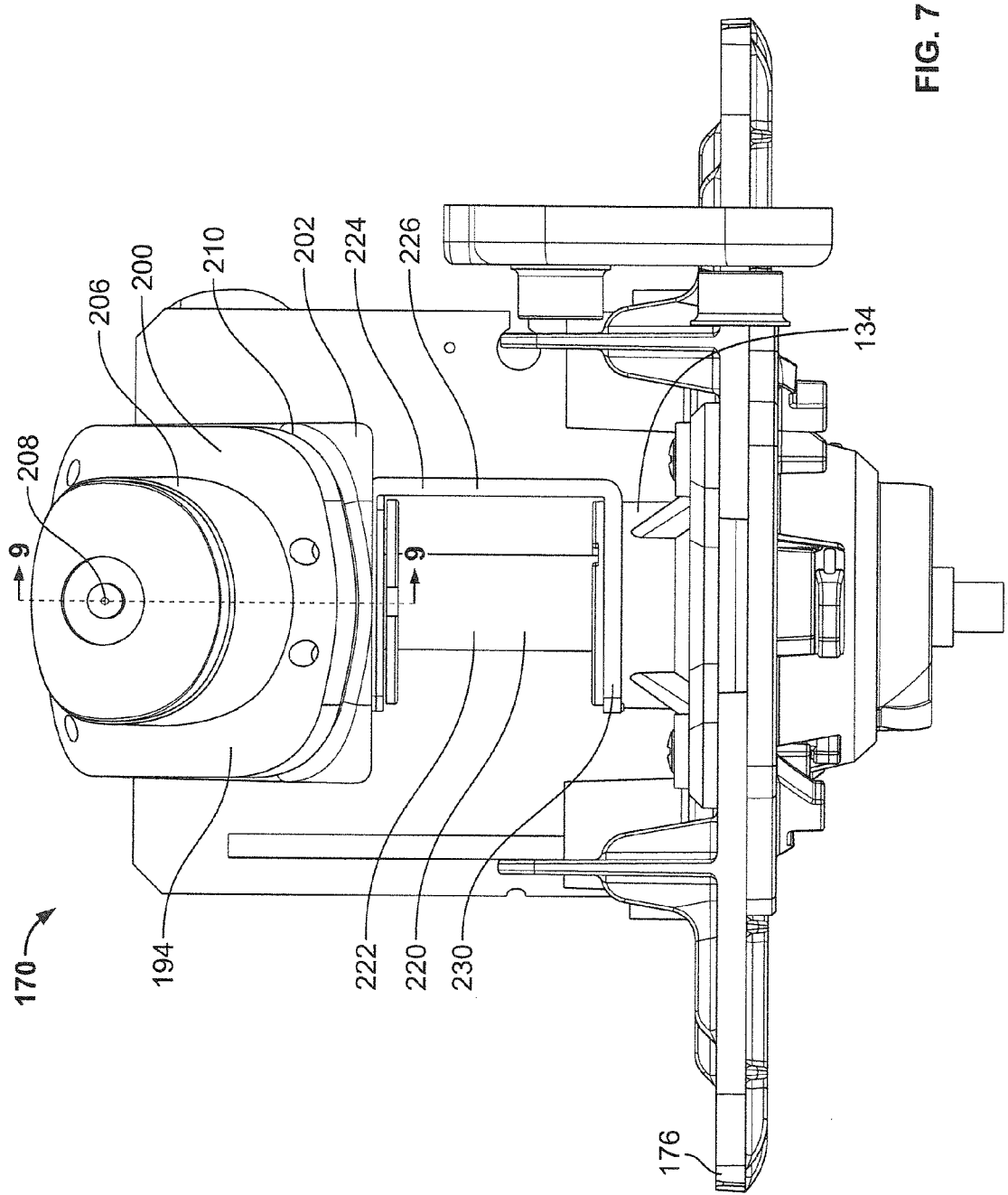
FIG. 7 is a front elevational view of the overcap of FIG. 6 with structures removed therefrom.
Figure 8:
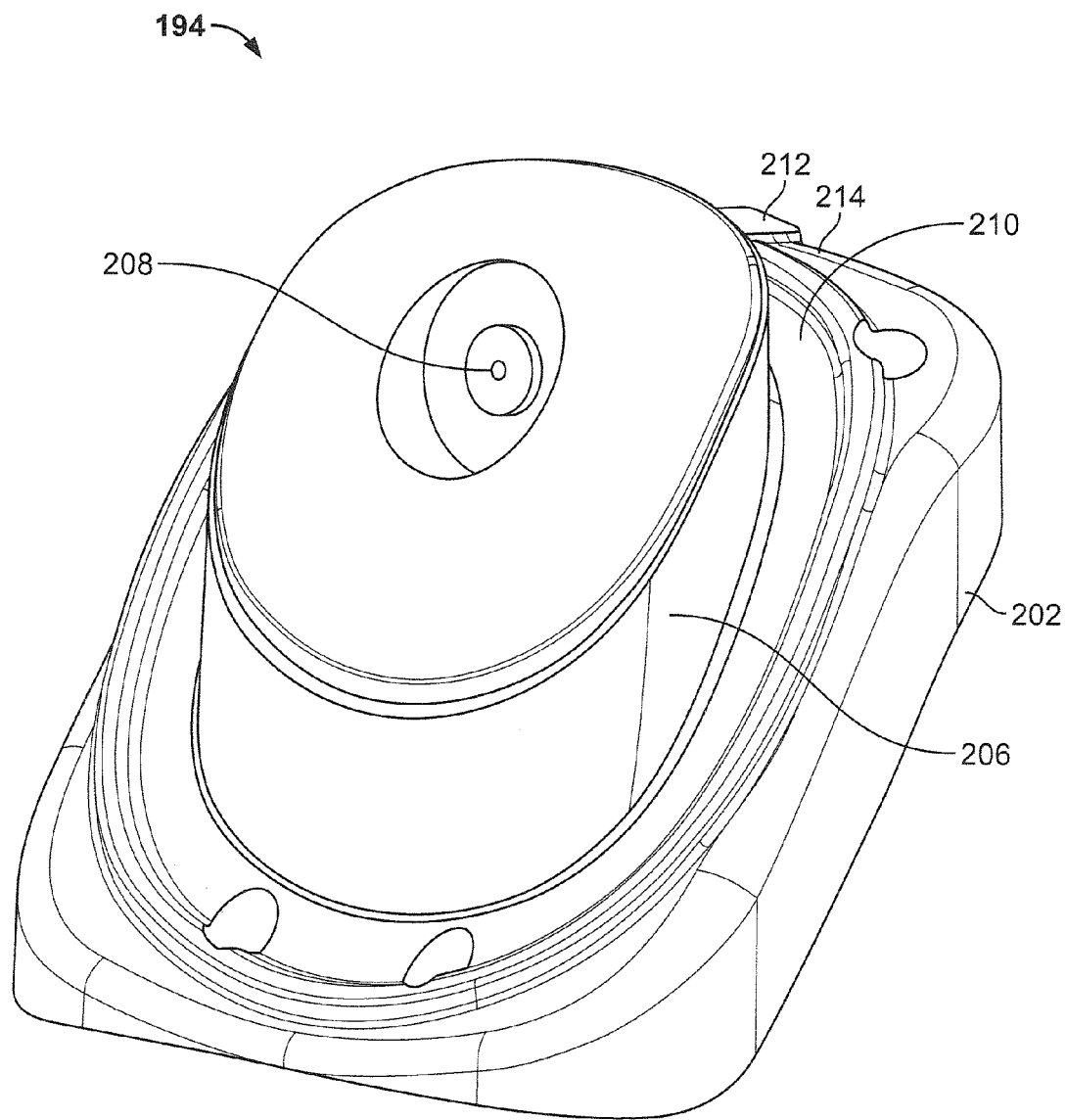
FIG. 8 is a front isometric view of the nozzle assembly of FIG. 1.
Figure 9:
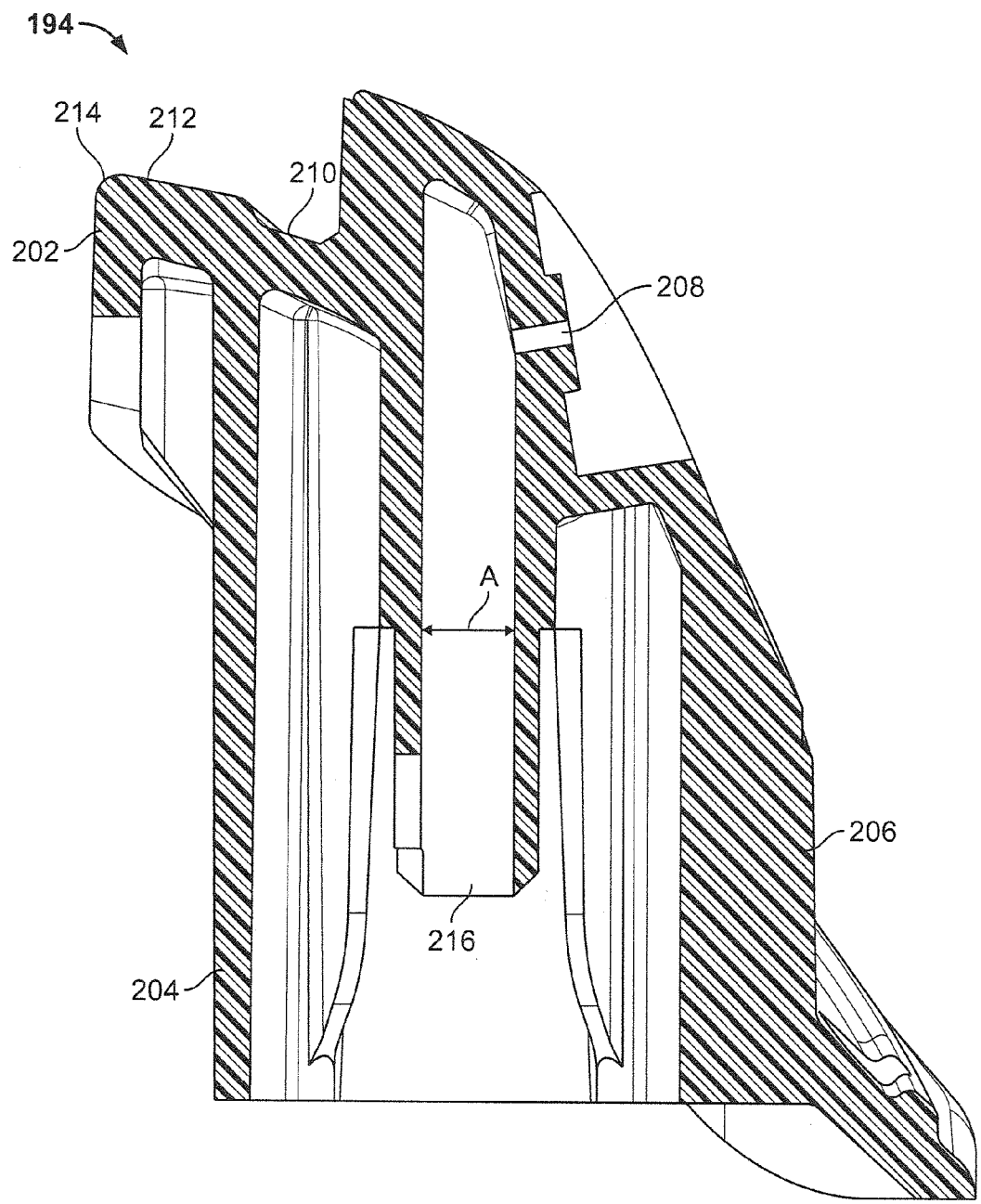
FIG. 9 is a cross-sectional view of the nozzle assembly of FIG. 8 taken generally along the lines 9-9 of FIG. 7.

Now turning to FIGS. 4 and 5, the overcap 104 is adapted to be attached to the container 102 of FIGS. 1-3 to form the product dispensing system 100. The overcap 104 includes an actuating system as described in more detail hereinbelow. A cylindrical chamber 170 (see FIG. 6) is defined between a contoured top wall 172 and a cylindrical sidewall 174, which tapers outwardly therefrom. The sidewall 174 extends downwardly toward a platform 176 (shown in FIGS. 6 and 7) and a bottom edge 178 of the sidewall 174. The platform 176 extends across the sidewall 174 in an area adjacent the bottom edge 178 to close the chamber 170 of the overcap 104. The chamber 170 is adapted to contain various parts of the product dispensing system 100 as will be explained in more detail hereinbelow.

Turning again to FIGS. 4 and 5, the bottom edge 178 of the overcap 104 circumscribes the sidewall 174 and is inset therefrom. The bottom edge 178 further includes a plurality of outwardly extending elongate ribs 180 disposed around an exterior surface thereof and adapted to interlock or otherwise interact with a housing (not shown) that may be optionally used with the dispensing system 100. As best seen in FIG. 4, the sidewall 174 of the overcap 104 further includes a switch 182 disposed on a rear face of the sidewall 174 adjacent the top wall 172. The switch 182 extends from a racetrack shaped opening 184 formed in the sidewall 174. The switch 182 is adapted to control various operational aspects of the product dispensing system 100. For example, the switch 182 may be used to set various time parameters, on/off modes, spray modes, and/or any other operational parameters as described in more detail hereinbelow.

As depicted in FIGS. 4 and 5, the contoured top wall 172 slopes downwardly from a first edge 190 adjacent the rear face toward a second edge 192 on an opposing front face of the overcap 104. The second edge 192 is disposed below the first edge 190. A nozzle assembly 194 is disposed adjacent a centerpoint 196 of the top wall 172 within a circular opening 198. The nozzle assembly 194 is adapted to allow the product 106 to be dispensed therethrough. The nozzle assembly 194 is surrounded by a flexible member in the form of a gasket 200

(see FIGS. 6 and 7) to prevent the leakage of product or volatile material through the opening 198.

Now turning to FIGS. 6-9, the nozzle assembly 194 extends downwardly into the chamber 170 of the overcap 104 and includes a contoured body 202 and a circular cylindrical sidewall 204 extending downwardly therefrom. A pedestal 206 protrudes upwardly from the body 202 and includes an opening 208 therein to allow product flow therethrough. The opening 208 is disposed in a recess formed in a central portion of the pedestal 206. The gasket 200 is adapted to rest on an upper surface 210 of the body 202 and surround the pedestal 206 (see FIGS. 8 and 9). A protrusion 212 extends upwardly from the upper surface 210 of the body 202 adjacent an edge 214 and is adapted to interact with and position the gasket 200 with respect to the body 202. Disposed within the sidewall 204 is a channel 216 extending partially or fully the length thereof. The channel 216 is adapted, together with the sidewall 204, to provide product communication between various internal dispensing components including a solenoid valve assembly 220 and the opening 208. The channel 216 is circular in cross-section for at least a portion of the length thereof, and a diameter A of the channel 216 at such portion is between about 0.5 mm to about 5 mm. The diameter of the opening 208 is selected to be between about 0.1 mm and about 1 mm.

Figure 12:
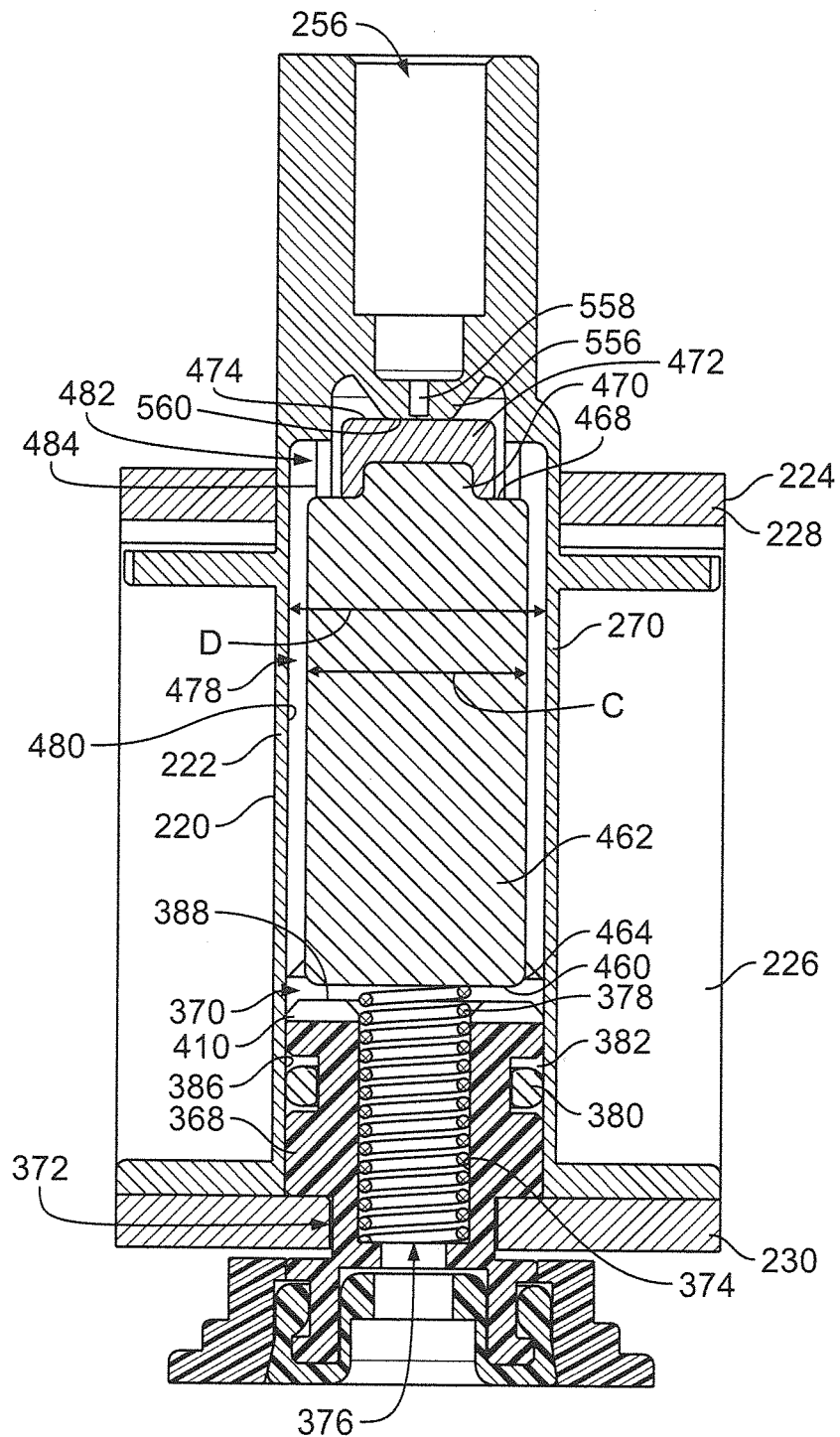
FIG. 12 is a cross-sectional view taken generally along the lines 12-12 of FIG. 10 illustrating the solenoid valve assembly.

Now turning to FIGS. 10-12, the solenoid valve assembly 220 includes a substantially cylindrical housing 222 supported by a C-shaped bracket 224 having a vertical sidewall 226 with an upper support member 228 and a lower support member 230 extending outwardly therefrom. The lower support member 230 of the C-shaped bracket 224 rests on the actuating member 134 (see FIGS. 16 and 17).

Figure 16:
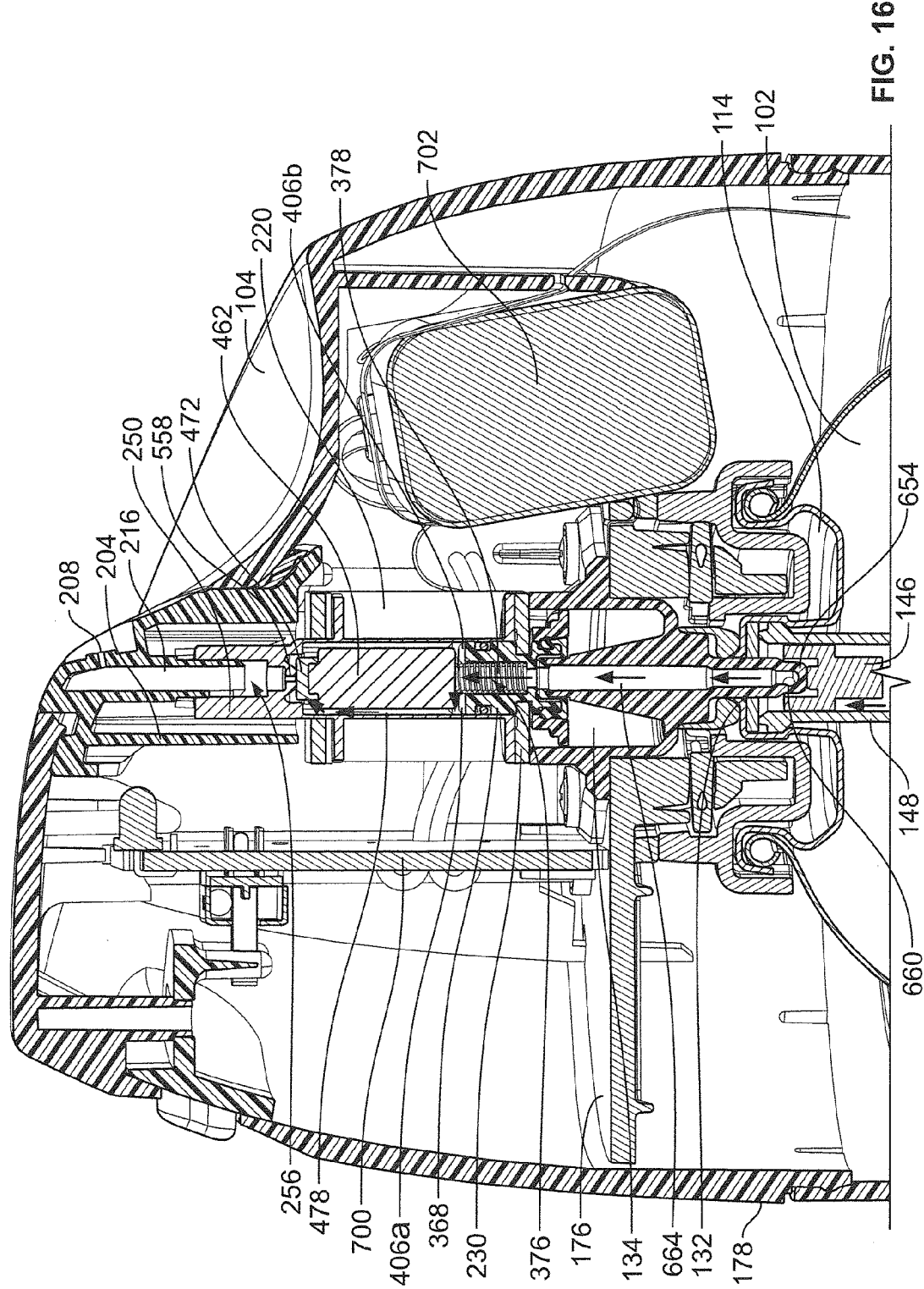
FIG. 16 is a fragmentary partial cross-sectional view of the product dispensing system in a first, or non-dispensing state.
Figure 17:
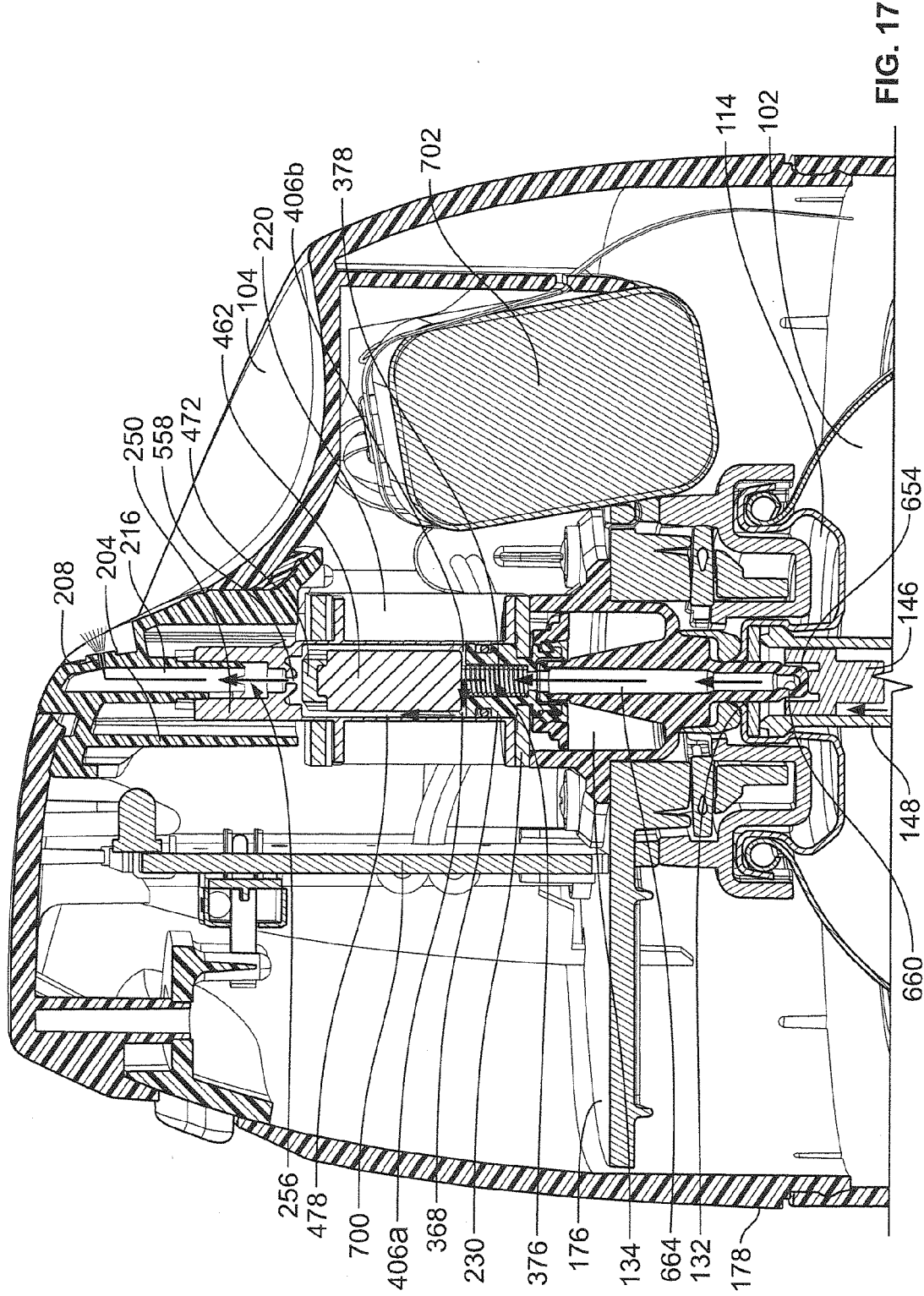
FIG. 17 is a fragmentary partial cross-sectional view of the product dispensing system of FIG. 16 in a second, or dispensing state.

Referring specifically to FIG. 10, the cylindrical housing 222 includes an upper portion 250 that extends upwardly through a top surface 252 of the upper support member 228 of the C-shaped bracket 224. The upper portion 250 includes a cylindrical sidewall 254 and an axial bore 255 together defining a conduit 256. Interior portions of the sidewall 204 of the nozzle assembly 194 surround and receive the upper portion 250 of the solenoid valve assembly 220 in an interference relationship (see also FIG. 9). Similarly, the axial bore 255 of the conduit 256 surrounds and receives structure defining the channel 216 of the nozzle assembly 194 in an interference relationship. The diameter B of the conduit 256 of the upper portion 250 is greater than the diameter A of the channel 216 of the sidewall 204. The upper portion 250 further includes an elongate axially extending rectilinear member 258 protruding from the sidewall 254 on a side thereof and a smaller rectilinear member 258' (see FIG. 11) on an edge thereof. As seen in FIGS. 16 and 17, the sidewall 204 and the channel 216 of the nozzle assembly 194 are fittingly engaged with the upper portion 250 of the housing 222 in order to attach the nozzle assembly 194 to the solenoid valve assembly 220 and provide a tight interference fit such that product cannot escape therefrom. In another embodiment, the nozzle assembly and solenoid valve assembly comprise an integral structure. In yet a different embodiment, the nozzle assembly is attached to the solenoid valve assembly in any manner known in the art so long as a substantially fluid-tight seal is created.

As best seen in FIGS. 10 and 11, the housing 222 further includes a medial portion 270 that extends downwardly from the upper portion 250. The medial portion 270 has a substantially uniform outer diameter between the upper support member 228 and lower support member 230 and terminates at a stepped lower portion 272 adjacent a bottom surface 274 of the lower support member 230 of the C-shaped bracket 224.

First and second annular flanges 280a, 280b surround an exterior surface 282 of the housing 222 in an area adjacent a lower surface 284 of the upper support member 228 and an area directly adjacent an upper surface 286 of the lower support member 230, respectively. Electrical winding coils 275 (partially shown in FIG. 10) extend about the medial portion 270 between the annular flanges 280a, 280b, which serve to constrain the coils 275 to the space therebetween. The first flange 280a is interrupted by two small rectangular cutouts 288 on opposing sides thereof. The second flange 280b includes two substantially rectangular channels 290 disposed in an upper surface 292 thereof. The channels 290 extend outwardly from opposing sides of the housing 222 toward an edge 294 of the second ring 280b. The rectangular cutouts 288 and/or channels 290 are provided to receive one or more wires.

Figures 13, 14:
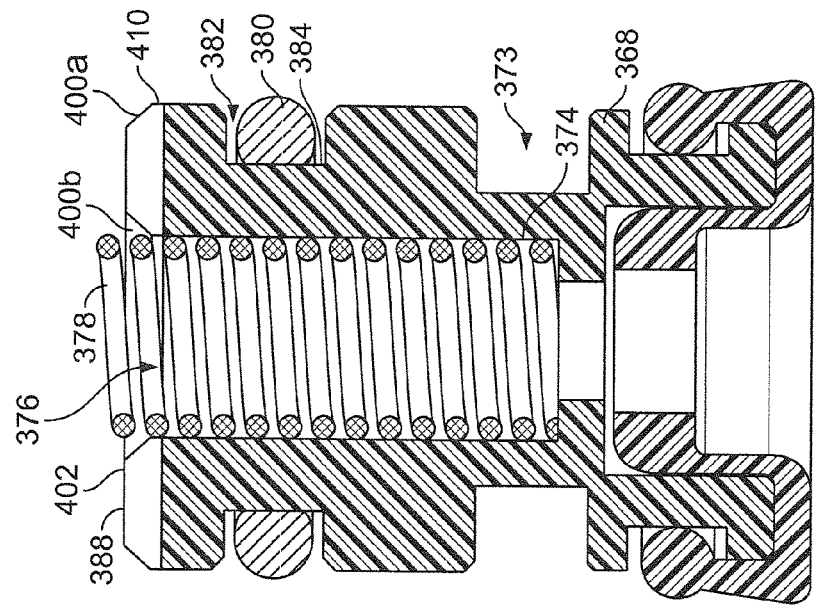
FIG. 13 is a top isometric view of the stopper of FIG. 12 with the O-ring and spring removed therefrom.
FIG. 14 is a cross-sectional view of the stopper, O-ring, and spring of FIG. 12 taken generally along the lines 14-14 of FIG. 13.

As best seen in FIG. 12, a stopper 368 is disposed in a cavity 370 within the housing 222. Referring also to FIGS. 13 and 14, the stopper 368 is preferably made of an elastomeric material, but may alternatively be made of a different material, such as a metal. The stopper 368 is captured by walls defining a slot 372 in the lower support member 230 of the C-shaped bracket 224. The walls extend into a circumferential groove 373 formed in the stopper 368 (see FIGS. 13 and 14). With reference to FIGS. 12 and 14, the stopper 368 includes an elongate substantially cylindrical stepped inner wall 374 that defines an axial elongate passage 376 within which a spring member 378 is disposed and supported. An elastomeric O-ring 380 is disposed in a further circumferential groove 382 and is compressed between a base wall 384 partially defining the groove 382 (see FIG. 14) and an inner wall 386 of the housing 222 (see FIG. 12) to seal the stopper 368 against the inner wall 386.

With particular reference to FIG. 13, the stopper 368 preferably includes a non-planar upper facing or confronting surface 388 including tapered external and internal surfaces 400a, 400b, respectively, extending downwardly from a top edge 402 of the stopper 368. The surface 388 is further interrupted by a non-planar surface in the form of one or more grooves disposed therein that define a flow pathway. In one embodiment, two rectilinear radial grooves 406a, 406b are disposed on opposing sides of the elongate passage 376 and extend from the stepped inner wall 374 defining the passage 376 toward an outer surface 410 of the stopper 368.

Each of the grooves 406a, 406b includes a length dimension L preferably between about 0.25 mm and about 5 mm, and more preferably between about 0.5 mm and about 3 mm, and most preferably about 1.75 mm. As shown in FIG. 13, each of the grooves 406a, 406b includes a width dimension W between about 0.25 mm and about 3 mm, and more preferably between about 0.25 mm and about 2 mm, and most preferably about 1 mm. Further, a height dimension H of the grooves 406a, 406b is between about 0.1 mm to about 2 mm, and more preferably between about 0.2 mm and about 1 mm, and most preferably about 0.5 mm. In the illustrated embodiment, the grooves 406a, 406b have substantially identical dimensions. In another embodiment, the grooves have different dimensions. In a still further embodiment, only a single groove is provided extending from the stepped inner wall 374 and in fluid communication therewith. In yet a different embodiment, grooves are provided in different shapes and sizes to provide differing product flow characteristics as desired. Still further, the upper confronting surface 388 may be a different non-planar shape, e.g., convex or concave, and may include one or more cavities (such as dimples), one or more projections or protuberances, or may have a wavy shape. In fact, any non-planar shape is contemplated that allows product flow out of the passage 376 even when the surface 388 is in contact with another surface, such as a lower facing or confronting surface 460 of a plunger 462 of the solenoid valve assembly 220 (see FIG. 15).

Figure 15A:
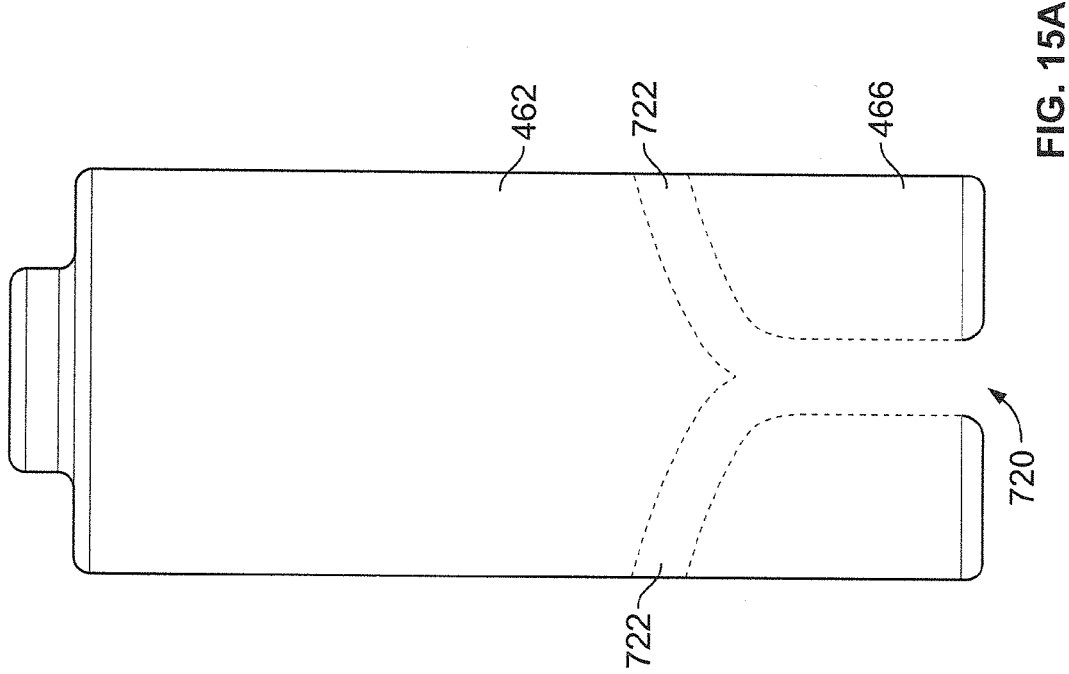
FIG. 15A is a side elevational view of a different embodiment of a plunger.
Figure 15:
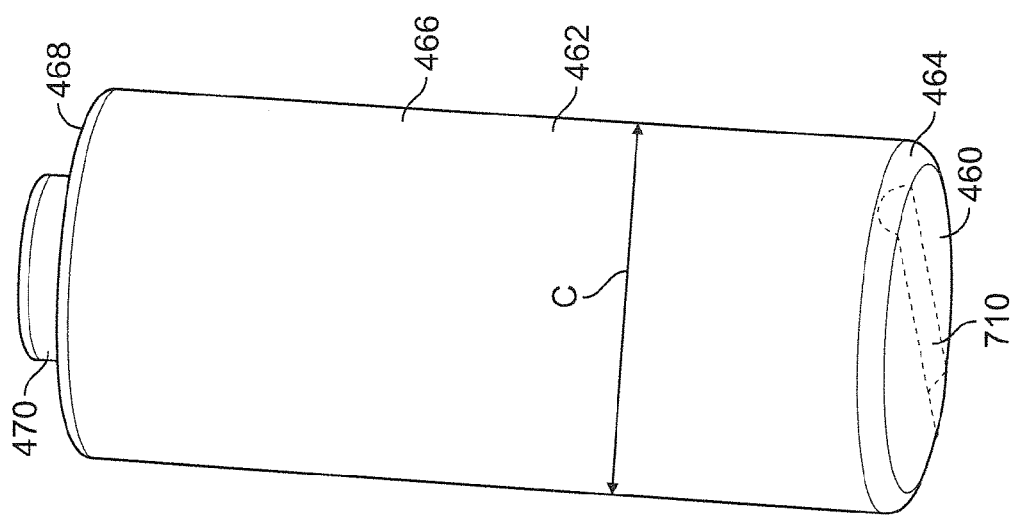
FIG. 15 is a bottom isometric view of the plunger of FIG. 12.

As seen in FIGS. 12 and 15, the plunger 462 is disposed above the spring 378 and the stopper 368 within the cavity 370. The plunger 462 serves as the armature of the solenoid valve assembly 220. In the illustrated embodiment, the lower surface 460 is substantially planar and may have a slightly tapered edge surface 464 therearound. The plunger 462 further comprises a cylindrical body 466 extending upwardly therefrom that terminates at an upper surface 468. A central portion 470 projects upwardly from the upper surface 468 of the plunger 462. A cover member 472 extends over and around the central portion 470 and includes a flat upper surface 474. A diameter C of the body 466 of the plunger 462 is smaller than a diameter D of the cavity 370. This difference in diameter creates a circumferential gap 478 between the plunger 462 and an inner wall 480 of the housing 222. The gap 478 further extends axially from an area adjacent the lower surface 460 toward an area adjacent the cover member 472. The gap 478 includes a widened portion 482 in the area adjacent the cover member 472 because the diameter of the cover member 472 is substantially smaller than the diameter of the body 466 of the plunger 462. A plurality of spaced ribs 484 extend axially along the inner wall 480 adjacent the plunger 462 in the gap 478 and the widened portion 482 of the gap 478. The ribs 484 are provided to center the plunger 462 and guide and direct the flow of product through the gap 478 and provide enhanced fluid dynamics for the solenoid valve assembly 220.

As best seen in FIG. 12, an inverted cone shaped wall 556 extends downwardly and includes a small orifice 558 therein. The orifice 558 is in fluid communication with the conduit 255. The cone shaped wall 556 includes a substantially planar central seating surface 560.

Although not shown, a metal cover encloses the various parts of the assembly 220. Also, magnetic material such as soft iron laminations may be provided in a flux path of the assembly 220 as is conventional.

Referring to FIG. 16, the actuating member 134 is secured to and extends through the platform 176 and is further in fluid communication with an orifice which is, in turn, in fluid communication with the axial passage 376. The nozzle assembly 194 extends upwardly from and is fittingly received in the solenoid valve assembly 220 as noted previously. The nozzle assembly 194 terminates at the opening 208. All of these components collectively provide a path for the fluid to flow from the container 102 upwardly through the overcap 104 and outwardly into the atmosphere.

More specifically, the overcap 104 and container 102 are secured together. In one embodiment, the overcap 104 and container 102 are attached via an interference or press fit. In another embodiment, the overcap 104 and container 102 are attached by adhesive. In yet another embodiment, the overcap 104 and container 102 are attached using, for example, any of the attachment mechanisms that are described in Demarest et al, U.S. patent application Ser. No. 13/021,685, entitled "Attachment Mechanism For A Container," which is owned by the assignee of the present application and which was filed on Feb. 4, 2011, and is hereby incorporated by reference in its entirety. Once the container 102 and overcap 104 are mated, a tip 654 of the actuating member 134 extends into the opening 132 of the mounting cup 114 of the container 102 and creates a sealing relationship therewith to form a fluid-tight seal.

As depicted by the arrows in FIGS. 16 and 17, pressurized product 106 leaves the opening 132 of the container 102 and travels through an opening 660 in the tip 654 of the actuating member 134 and through a fluid flow channel 664 of the actuating member 134. The product 106 then moves upwardly into the solenoid valve assembly 220, through the passage 376 of the stopper 368 and laterally outwardly through the grooves 406a, 406b. The product 106 then travels axially through the gap 478 adjacent the plunger 462 until reaching the member 472. As shown in FIG. 16, when the solenoid valve assembly 220 is in a de-energized state, the member 472 forms a fluid-tight seal with the seating surface to block product flow through the orifice 558. Once the solenoid valve assembly 220 is energized, the plunger 462 of the solenoid valve assembly 220 moves axially downwardly against the force of the spring 378. At the same time, the member 472 moves away from the seating surface to allow product flow therethrough, as shown in FIG. 17. After the solenoid valve assembly is de-energized, the plunger 462 is moved axially upwardly by the spring 378 and the member 472 again seals against the surface to block product flow through the orifice 558. At this point, product 106 is trapped through the various fluid flow paths of the product dispensing system 100 as described herein, and is unable to escape.

In use, the product dispensing system 100 is adapted to release a product from the container 102 upon the occurrence of a particular condition. The condition could be the manual activation of the overcap 104 or the automatic activation of the overcap 104 in response to an electrical signal from a timer or a sensor. In this regard, a controller is carried by a printed circuit board 700 powered by a battery 702 (FIGS. 6, 16, and 17) to control the solenoid assembly 220, preferably in response to the position of the switch 182. The product discharged may be a fragrance or insecticide or other volatile disposed within a carrier liquid or other substance, a deodorizing liquid, or the like. The product may also or alternatively comprise other actives, such as sanitizers, air fresheners, odor eliminators, mold or mildew inhibitors, insect repellents, medicaments, cleaning agents, aromatherapeutic materials, or the like. The product alternatively may comprise any solid, liquid, gas, and/or combinations thereof known to those skilled in the art that may be dispensed from a container. The product dispensing system 100 is therefore adapted to dispense any number of different formulations.

In a different embodiment the upper surface 388 of the stopper 368 is planar or non-planar and the lower confronting surface 460 is non-planar. Specifically, the lower confronting surface 462 may include one or more groove(s) 710 that define a flow pathway as seen in dashed lines in FIG. 15. The groove(s) 710 may be replaced by one or more other structures, such as protuberances or dimples, or may be concave and/or convex or wavy in shape, as noted above in connection with the surface 388. In use, the product 106 of the product dispensing system 100 is able to travel through the solenoid valve assembly 220 utilizing the at least one groove 700 in the bottom surface 460 of the plunger 462 as a flow path during periods of extended actuation.

In still a further embodiment, the upper surface 388 of the stopper 368 is planar or non-planar and the plunger 462 further comprises at least one bore 720 extending at least partially therethrough and terminating at one or more lateral openings 722, e.g., as shown in FIG. 15A. The bore(s) 720 may be provided centrally through the cylindrical body 466 or offset therefrom. Preferably, the bore 720 extends substantially upwardly and diverges at an angle therefrom, e.g., in a Y-like shape as shown in FIG. 15A. The angle at which the bore 720 extends outwardly is preferably selected to provide for a product flow path that maximizes the product fluid dynamics through the product dispensing system 100. For example, it is contemplated that the bore 720 extends upwardly and extends outwardly toward the openings 722 so as to avoid a sharp angle, which may slow the product flow through the dispensing system 100. Further, while the bore 720 is depicted as including two openings 722, it should be apparent that any number of openings can be provided at various points along the plunger 462 so long as a fluid flow path is maintained through the stopper 368 and the plunger 462.

Several modes of dispensing the product 106 are included in this disclosure. It is specifically contemplated that the modes of dispensing are selected to control the amount of product dispensed for a specific purpose. For example, in a product dispensing system 100 that includes an insecticide, the mode of dispensing may be selected to provide an initial burst that kills insects in the surrounding area, followed by a second burst that maintains the concentration of the insecticide to deter further insects from entering the surrounding area. Any of the modes of dispensing presented herein may be implemented utilizing any of the embodiments of the product dispensing system 100 and more specifically, any of the embodiments of the solenoid valve assembly 220 presented herein. Further, the modes of dispensing disclosed herein may be utilized with any other apparatuses adapted to dispense a product.

In a first mode of dispensing, the product 106 is emitted in a plurality of stages having unequal intensities that last for unequal emission periods. The intensity of the emission is dictated by the duration of the on-time of the solenoid valve assembly 220 in combination with the frequency of activation of the on-time. The emission period comprises the time that the dispensing device 100 is operating in a specific stage.

One illustrative example implementing the first mode of dispensing includes a two-stage emission cycle, wherein the product 106 is continuously emitted during a first stage that includes releasing the product at a higher intensity for a shorter emission period as compared to a second stage in which the product is emitted with a lower intensity for a longer emission period as compared to the first stage. More specifically, the first stage is adapted to provide an initial burst of a higher concentration of the product and the second stage is adapted to maintain the chemical concentration of the product after the completion of the first stage. During the first stage, the solenoid valve assembly 220 has an on-time of between about 75 ms to about 250 ms, and more preferably about 100 ms to about 225 ms, and most preferably about 130 ms to about 200 ms. In the first stage, the solenoid valve assembly 220 is preferably energized between about every 5 seconds to about every 60 seconds, and more preferably about every 10 seconds to about every 30 seconds, and most preferably about every 20 seconds. Still further, the first stage preferably has an emission period of between about 10 minutes to about 60 minutes, and more preferably about 20 minutes to about 40 minutes, and most preferably about 30 minutes.

The first mode of dispensing further includes the second stage that is adapted to immediately follow the first stage. During the second stage, the solenoid valve assembly 220 has an on-time of between about 10 ms to about 150 ms, and more preferably about 30 ms to about 100 ms, and most preferably about 40 ms to about 80 ms. In the second stage, the solenoid valve assembly 220 is preferably energized for a time period greater than about 20 seconds. More specifically, the solenoid valve assembly 220 is preferably energized between about every 20 seconds to about every 500 seconds, and more preferably about every 20 seconds to about every 300 seconds, and most preferably about every 20 seconds to about every 100 seconds. The emission period for the second stage is preferably between about 60 minutes to about 300 minutes, and more preferably about 100 minutes to about 250 minutes, and most preferably about 150 minutes to about 210 minutes.

In use, the first mode of dispensing is implemented in an automatic manner such that a user is able to select the first mode of dispensing by way of the switch 182 of the product dispensing system 100. After the user slides the switch 182 to the first dispensing mode, for example, the controller of the product dispensing system 100 operates the solenoid valve assembly 220 in accordance with the first stage and immediately thereafter in accordance with the second stage. At the end of the second stage, the product dispensing system 100 may cycle to the first stage again and/or cycle into a different mode of dispensing. Still further, a dwell period may be provided before, during, and/or after either the first and/or second stages.

In a second mode of dispensing, the product 106 is emitted in a single stage that operates over a pre-defined emission period. In one embodiment, the emission period is between about 1 hour to about 20 hours, and more preferably from about 5 hours to about 15 hours, and most preferably about 12 hours. In this embodiment, the emission period is preferably followed by a dwell period of about 1 hour to about 20 hours, and more preferably from about 5 hours to about 15 hours, and most preferably about 12 hours. The second mode of dispensing may include an emission period of about 12 hours and a dwell period of about 12 hours. In a different embodiment, the second mode of dispensing includes an emission period of about 24 hours or longer. In this embodiment, the emission period may be continuous, i.e., followed by another emission period, or the emission period may be followed by a dwell period.

In one embodiment, the intensity of the second mode of dispensing is the same no matter the length of the emission period. More specifically, the solenoid valve assembly 220 has an on-time of between about 1 ms to about 100 ms, and more preferably between about 5 ms and about 50 ms, and most preferably about 21 ms. The solenoid valve assembly 220 is preferably energized between about every 1 minute to about every 30 minutes, and more preferably about every 3 minutes to about every 13 minutes, and most preferably about every 7 minutes. In a different embodiment, the intensity of the second mode of dispensing varies according to the length of the emission period. It should be apparent to one having skill in the art that the solenoid on-time, emission period, and dwell period parameters may be modified to provide for a specifically desired product intensity.

The on-time of the solenoid valve assembly 220 may be widely varied without the usual concern regarding flow interruption at longer on-times. In another embodiment, one or more actuation cycle(s) may alternate between longer bursts and shorter bursts. In all of the aforementioned embodiments, extended actuation is possible due to the non-planar confronting surface(s) of one or both of the plunger and/or stopper disposed within the solenoid valve assembly.

While the embodiments disclosed herein are generally described in connection with the container 102 and the overcap 104, it is intended that the solenoid valve assembly 220 may be used with any conventional container and/or overcap. It is specifically contemplated that the solenoid valve assembly 220 may be used with either male valve stern activated containers or female valve stem activated containers of the axially-operated and/or tilt-operated type. Alternatively, any pressurized container having a valve assembly may be used in connection with any of the disclosed embodiments and it will be readily apparent to one of ordinary skill how such containers may be used with the embodiments described with particularity herein.

INDUSTRIAL APPLICABILITY

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

We claim:

1. A solenoid valve assembly adapted to control product flow through a dispensing system, the solenoid valve assembly comprising:
   a housing;
   a plunger disposed within the housing and having a first axial surface;
   a stopper disposed within the housing and having a second axial surface facing the first axial surface; and
   at least one flow pathway provided on at least one of the first and second axial surfaces when the first and second axial surfaces are in contact with one another.

2. The solenoid valve assembly of claim 1, wherein the at least one flow pathway includes at least one groove extending through the first axial surface.

3. The solenoid valve assembly of claim 1, wherein the at least one flow pathway includes at least one groove extending through the second axial surface.

4. The solenoid valve assembly of claim 1, wherein a gap is provided between the plunger and the housing, the gap being adapted to allow product flow therearound.

5. The solenoid valve assembly of claim 1, wherein an axial elongated passage is provided through the stopper, the axial elongated passage adapted to allow product to flow through the stopper.

6. The solenoid valve assembly of claim 1, wherein the stopper includes a plurality of rings extending outwardly therefrom.

7. The solenoid valve assembly of claim 1, wherein the solenoid valve assembly is adapted to interact with an actuating member.

8. The solenoid valve assembly of claim 1, wherein an opening is provided in an upper wall of the housing adapted to allow product flow therethrough.

9. The solenoid valve assembly of claim 1, which is activated according to a mode of dispensing that includes a first stage in which the solenoid valve assembly has an on-time of between about 75 ms to about 250 ms and a second stage in which the solenoid valve assembly has an on-time of between about 10 ms to about 150 ms.

10. The solenoid valve assembly of claim 9, wherein the mode of dispensing further includes an emission period of between about 10 minutes to about 60 minutes in the first stage and an emission period of between about 60 minutes to about 300 minutes in the second stage.

11. The solenoid valve assembly of claim 1, which is activated according to a mode of dispensing that includes a predefined emission period, in which the solenoid valve assembly has an on-time of between about 1 ms to about 100 ms.

12. A product dispensing system, comprising:
   a container having a product therein;
   an overcap releasably attached thereto; and
   a solenoid valve assembly adapted to control product flow through a dispensing system, the solenoid valve assembly comprising:
      a housing;
      a plunger disposed within the housing and having a first axial surface;
      a stopper disposed within the housing and having a second axial surface facing the first axial surface; and
      at least one flow pathway provided on at least one of the first and second axial surfaces when the first and second axial surfaces are in contact with one another.

13. The product dispensing system of claim 12, further including a nozzle assembly attached to the solenoid valve assembly.

14. The product dispensing system of claim 12, further including an actuating member extending downwardly from the overcap and adapted to interact with the container.

15. The product dispensing system of claim 12, wherein the at least one flow pathway includes at least one groove extending through at least one of the first and second axial surfaces.

16. A method of dispensing a product, the method comprising the steps of:
   providing a solenoid valve assembly including:
      a housing;
      a plunger disposed within the housing and having a first axial surface;
      a stopper disposed within the housing and having a second axial surface facing the first axial surface; and
      at least one flow pathway provided on at least one of the first and second axial surfaces when the first and second axial surfaces are in contact with one another;
   providing a product within a container in communication with the solenoid valve assembly;
   providing a switch adapted to control the actuation of the solenoid valve assembly; and
   activating the switch to dispense the product through the solenoid valve assembly.

17. The method of claim 16, further including the step of providing an axial elongated passage through the stopper to allow product to flow through the stopper.

18. The method of claim 16, further including the step of providing an actuating member extending from an overcap adapted to interact with the container.

19. The method of claim 18, further including the step of opening a valve within the container utilizing the actuating member.

20. The method of claim 16, further including the step of providing the switch with multiple switch settings to control various operational parameters.

* * * * *